US006972041B1

(12) United States Patent
Stone (10) Patent No.: US 6,972,041 B1
(45) Date of Patent: *Dec. 6, 2005

(54) BONE XENOGRAFTS (75) Inventor: Kevin R. Stone, Mill Valley, CA (US)

(73) Assignee: CrossCart, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/646,376

(22) PCT Filed: Mar. 15, 1999

(86) PCT No.: PCT/US99/05661

§ 371 (c)(1),
(2), (4) Date: Sep. 14, 2000

(87) PCT Pub. No.: WO99/47080

PCT Pub. Date: Sep. 23, 1999

Related U.S. Application Data (60) Provisional application No. 60/078,139, filed on Mar. 16, 1998, provisional application No. 60/100,755, filed on Sep. 17, 1998.

(51) Int. Cl.$^7$ ................................................ A61F 2/02
(52) U.S. Cl. .............................. 623/23.72; 623/11.11; 623/23.63
(58) Field of Search .......................... 623/11.11, 13.11, 623/13.17, 16.11, 23.63, 23.72, 2.42, 2.1, 623/23.76, 23.75; 435/325, 1.1, 1.3; 424/423, 424/422, 548, 549

(56) References Cited

U.S. PATENT DOCUMENTS 4,400,833 A * 8/1983 Kurland
4,585,585 A 4/1986 Waite .................. 260/112.5 R
4,597,266 A 7/1986 Entrekin ........................ 62/46
4,609,627 A 9/1986 Goldstein ................... 435/269
4,627,853 A 12/1986 Campbell et al. ............. 623/16

(Continued)

FOREIGN PATENT DOCUMENTS

EP          347496        12/1989

(Continued)

OTHER PUBLICATIONS

Rodrigo et al., "Osteocartilaginous Allografts as Compared with Autografts in the Treatment of Knee Joint Osteocartilaginous Defects in Dogs", Clinical Orthopedics and Related Research, 134, pp. 342-349 (1978).

(Continued)

*Primary Examiner*—Pedro Philogene
(74) *Attorney, Agent, or Firm*—McDermott Will & Emery LLP (57) ABSTRACT

The invention provides an article of manufacture comprising a substantially non-immunogenic bone xenograft for implantation into humans. The invention further provides a method for preparing a bone xenograft by removing at least a portion of a bone from a non-human animal to provide a xenograft (X); washing the xenograft in saline and alcohol; subjecting the xenograft to a cellular disruption treatment; and treating the xenograft with a glycosidase to remove surface carbohydrate moieties. The invention also provides an article of manufacture produced by the above identified method of invention. The invention further provides a bone xenograft for implantation into a human including a portion (10) of a bone from a nonhuman animal, wherein the portion has substantially no surface carbohydrate moieties which are susceptible to glycosidase digestion. Each xenograft of the invention has substantially the same mechanical properties as a corresponding native bone.

46 Claims, 1 Drawing Sheet

U.S. PATENT DOCUMENTS

| | | | |
|---|---|---|---|
| 4,642,120 A | 2/1987 | Nevo et al. | 623/16 |
| 4,678,470 A | 7/1987 | Nashef et al. | 623/16 |
| 4,755,593 A | 7/1988 | Lauren | 530/356 |
| 4,789,663 A | 12/1988 | Wallace et al. | 514/21 |
| 4,801,299 A | 1/1989 | Brendel et al. | 623/1 |
| 4,880,429 A | 11/1989 | Stone | 623/18 |
| 4,932,973 A | 6/1990 | Gendler | 623/16 |
| 5,067,962 A | 11/1991 | Campbell et al. | 623/13 |
| 5,071,741 A | 12/1991 | Brockbank | 435/1 |
| 5,131,850 A | 7/1992 | Brockbank | 435/1 |
| 5,160,313 A | 11/1992 | Carpenter et al. | 600/36 |
| 5,171,660 A | 12/1992 | Carpenter et al. | 435/1 |
| 5,192,312 A * | 3/1993 | Orton | |
| 5,206,023 A | 4/1993 | Hunziker | 424/423 |
| 5,216,126 A | 6/1993 | Cox et al. | 530/350 |
| 5,306,304 A | 4/1994 | Gendler | 623/16 |
| 5,333,626 A | 8/1994 | Morse et al. | 128/898 |
| 5,516,532 A * | 5/1996 | Atala et al. | |
| 5,613,982 A | 3/1997 | Goldstein | 623/11 |
| 5,632,778 A | 5/1997 | Goldstein | 623/11 |
| 5,681,353 A | 10/1997 | Li et al. | 623/18 |
| 5,782,915 A | 7/1998 | Stone | 623/11 |
| 5,865,849 A | 2/1999 | Stone | 623/18 |
| 5,902,338 A | 5/1999 | Stone | 623/13 |
| 5,904,716 A | 5/1999 | Gendler | 623/11 |
| 5,922,027 A | 7/1999 | Stone | 623/11 |
| 5,944,755 A | 8/1999 | Stone | 623/16 |
| 5,984,858 A | 11/1999 | Stone | 600/20 |
| 6,046,379 A | 4/2000 | Stone et al. | 623/11 |
| 6,049,025 A | 4/2000 | Stone et al. | 128/898 |
| 6,110,206 A | 8/2000 | Stone | 623/13.11 |
| 6,113,603 A * | 9/2000 | Medoff | |
| 6,231,608 B1 * | 5/2001 | Stone | 623/16.11 |

FOREIGN PATENT DOCUMENTS

| | | |
|---|---|---|
| WO | WO 84/03036 | 8/1984 |
| WO | WO 95/26740 | 10/1995 |
| WO | WO 95/28412 | 10/1995 |
| WO | WO 95/33828 | 12/1995 |

OTHER PUBLICATIONS

Webber et al., "Cell Culture of Rabbit Meniscal Fibrochondrocytes: Proliferative and Synthetic Response to Growth Factors and Ascorbate", Journal of Orthopedic Research, 3, pp. 36-42 (1985).

Collins et al., "Characterization of Porcine Endothelial Cell Determinants Recognized by Human Natural Antibodies", Xenotransplantation, 1, pp. 36-46 (1994).

LaVecchio et al., "Enzymatic Removal of Alpha-Galactosyl Epitopes From Porcine Endothelial Cells Diminishes The Cytotoxic Effect of Natural Antibodies", Transplantation, 60, pp. 841-847 (1995).

Cotterell et al., "The Humoral Immune Response in Humans Following Cross-Perfusion of Porcine Organs", Transplantation, 60, pp. 861-868 (1995).

Galili, "Interaction of the Natural Anti-Gal Antibody with α-Galactosyl Epitopes: a Major Obstacle for Xenotransplantation in Humans", Immunology Today, 14, pp. 480-482 (1993).

Elves et al., "An Investigation Into The Immunogenicity Of Various Components of Osteoarticular Grafts", The British Journal of Experimental Pathology, 55, pp. 344-351 (1974).

Derby et al., "The Histochemical Specificity of Streptomyces Hyaluronidase and Chondroitinase ABC", Histochemical Journal, 10, pp. 529-547 (1978).

Homandberg et al., "High Concentrations of Fibronectin Fragments Cause Short-Term Catabolic Effects in Cartilage Tissue While Lower Concentrations Cause Continuous Anabolic Effects", Archives of Biochemistry and Biophysics, 311:2, pp. 213-218 (1994).

Homandberg et al., "Agents That Block Fibronectin Fragment-Mediated Cartilage Damage Also Promote Repair", Inflamm. Res., 46, pp. 467-471 (1997).

Homandberg et al., "Exposure of Cartilage to a Fibronectin Fragment Amplifies Catabolic Processes While Also Enhancing Anabolic Processes to Limit Damage", Journal of Orthopaedic Research, 16, pp. 237-246 (1998).

Homandberg et al., "Association of Proteoglycan Degradation with Catabolic Cytokine and Stromelysin Release from Cartilage Cultured with Fibronectin Fragments", 334:2, pp. 325-331 (1996).

Lipman et al., "Xenografts of Articular Chondrocytes in the Nude Mouse", Calcif. Tissue Int., 35, pp. 767-772 (1983).

Stone et al., "Porcine and Bovine Cartilage Transplants in Cynomolgus Monkey: I. A Model for Chronic Xenograft Rejection", Transplantation, 63, pp. 640-645 (1997).

Galili et al., "Porcine and Bovine Cartilage Transplants in Cynomolgus Monkey: II. Changes in Anti-Gal Response During Chronic Rejection", Transplantation, 63, pp. 646-651 (1997).

Stedman's Medical Dictionary, Williams & Wilkins, 26 ed., pp. 221, 793, 1070, 1966 (1995).

Galili et al., "Man, Apes, and Old World Monkeys Differ from Other Mammals in the Expression of α-Galactosyl Epitopes on Nucleated Cells", J. Biol. Chem., 263, 17755-17762 (1988).

J.M. Lane, et al., "Current Approaches to Experimental Bone Grafting", Orthopedic Clinics of North America 18, pp. 213-225 (1987).

U. Galili et al., "Interaction Between Human Natural Anti-α-Galactosyl Immunoglobulin G and Bacteria of The Human Flora", Infect. Immun. 56, 1730-1737 (1988).

R.M. Hamadeh et al., "Human Natural Anti-Gal IgG Regulates Alternative Complement Pathway Activation on Bacterial Surfaces", J. Clin. Invest. 89, 1223-1235 (1992).

M. Sandrin et al., "Anti-Pig IgM Antibodies in Human Serum React Predominantly With Gal (α1-3) Gal Epitopes", Proc. Natl. Acad. Sci USA 90, 11391-11395 (1993).

H. Good et al., "Identification of Carbohydrate Structures That Bind Human Antiporcine Antibodies: Implications for Discordant Xenografting In Humans", Transplant. Proc. 24, 559-562 (1992).

B.H. Collins, et al., "Cardiac Xenografts Between Primate Species Provide Evidence for the Importance of the α-Galactosyl Determinant in Hyperacute Rejection", J. Immunol. 154, 5500-5510 (1995).

S. Stevenson et al., "The Effect of Osteogenin (a Bone Morphogenetic Protein) on the Formation of Bone In Orthotopic Segmental Defects in Rats", Journal of Bone and Joint Surgery No. 76, 1676-1687 (1994).

J. Feighan, et al., "Induction of Bone by a Demineralized Bone Matrix Gel: A Study in a Rat Femoral Defect Model", Journal of Orthopaedic Research 13, 881-891 (1995).

R.G. Spiro et al., "Occurrence of α-D-Galactosyl Residues in the Thyroglobulin from Several Species. Localization in the Saccharide Chains of the Complex Carbohydrate Units", J. Biol. Chem. 259, 9858-9866 (1984).

R.G. Arumugham et al., "Structures of the Asparagine-Linked Sugar Chains of Laminin.", Biochem. Biophys. Acta 883, 112-126 (1986).

* cited by examiner

BONE XENOGRAFTS

This application is a 371 of PCT/US99/05661 filed Mar. 15, 1999, which claims benefit of Ser. No. 60/078,136 filed Mar. 16, 1998, and claims benefit of Ser. No. 60/100,755 filed Sep. 17, 1998.

FIELD OF THE INVENTION

The present invention relates to the field of bone transplantation, and in particular, to replacement and repair of damaged or defective human bone using a substantially immunologically compatible bone from a non-human animal.

BACKGROUND OF THE INVENTION

Human bone, a hard connective tissue consisting of cells embedded in an extracellular matrix of mineralized ground substance and collagen fibers, (Stedman's Medical Dictionary, Williams & Wilkins, Baltimore, Md. (1995)), is the most frequently transplanted tissue in humans. J. M. Lane et al. Current Approaches to Experimental Bone Grafting, 18 *Orthopedic Clinics of North America* (2) 213 (1987). In the United States alone more than 100,000 bone graft or implant procedures are performed every year to repair or to replace osseous defects resulting from trauma, infection, congenital malformation, or malignancy. Id.

Bone grafts and implants are often formed of autologous bone. Id. Transplantable autologous bone tissue for large defects, particularly in children, is often unavailable, however. Id. In addition, autologous bone transplantation may result in postoperative morbidity such as pain, hemorrhage, wound problems, cosmetic disability, infection or nerve damage at the donor site. Id. Further, difficulties in fabricating the desired functional shape from the transplanted autologous bone tissue may result in less than optimal filling of the bone defect. Id.

Alternatively, much of the structure and many of the properties of original bone tissue may be retained in transplants through use of heterograft or xenograft materials, that is, tissue from a different species than the graft recipient. In the area of soft tissues, for example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel xenografts are disclosed in WO 84/03036. None of these disclosures describe the use of a xenograft for bone replacement, however.

Once implanted in an individual, a xenograft provokes immunogenic reactions such as chronic and hyperacute rejection of the xenograft, however. In particular, bone xenografts may result in increased rates of fracture, resorption and nonunion secondary to immunologic rejection.

The term "chronic rejection", as used herein, refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular and/or extracellular matrices of the xenograft. For example, transplantation of cartilage xenografts from nonprimate mammals (e.g., porcine or bovine origin) into humans is primarily prevented by the interaction between the IgG natural anti-Gal antibody present in the serum of humans with the carbohydrate structure Galα1–3 Galβ1–4G1cNAc-R (α-galactosyl or α-gal epitope) expressed in the xenograft. K. R. Stone et al., *Porcine and bovine cartilage transplants in cynomolgus monkey: I. A model for chronic xenograft rejection*, 63 Transplantation 640–645 (1997); U. Galili et al., *Porcine and bovine cartilage transplants in cynomolgus monkey: II. Changes in anti-Gal response during chronic rejection*, 63 Transplantation 646–651 (1997). In chronic rejection, the immune system typically responds within one to two weeks of implantation of the xenograft.

In contrast with "chronic rejection", "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "extracellular matrix or matrices", as used herein, refer to an extracellular bone matrix of mineralized ground substance and collagen fibers. Stedman's Medical Dictionary, Williams & Wilkins, Baltimore, Md. (1995).

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic bone xenograft for implantation into a human in need of bone repair or replacement. The invention further provides methods for processing xenogeneic bone with reduced immunogenicity but with substantially native elasticity and load-bearing capabilities for xenografting into humans.

As used herein, the term "xenograft" is synonymous with the term "heterograft" and refers to a graft transferred from an animal of one species to one of another species. Stedman's Medical Dictionary, Williams & Wilkins, Baltimore, Md. (1995).

As used herein, the term "xenogeneic", as in xenogeneic graft, bone, etc., refers to a graft, bone, etc., transferred from an animal of one species to one of another species. Id.

The methods of the invention, include, alone or in combination, treatment with radiation, one or more cycles of freezing and thawing, treatment with a chemical cross-linking agent, treatment with alcohol or ozonation. In addition to or in lieu of these methods, the methods of the invention include a cellular disruption treatment and optionally glycosidase digestion of carbohydrate moieties of the xenograft optionally followed by treatment of carbohydrate moieties of the xenograft with capping molecules. Still another method of the invention includes cellular disruption and sterilization treatments. After one or more of the above-described processing steps, the methods of the invention provide a xenograft having substantially the same mechanical properties as a native bone.

As used herein, the term "cellular disruption" as in, for example, cellular disruption treatment, refers to a treatment for killing cells.

As used herein, the term "capping molecule(s)", refers to molecule(s) which link with carbohydrate chains such that the xenograft is no longer recognized as foreign by the subject's immune system.

In one embodiment, the invention provides an article of manufacture comprising a substantially non-immunogenic bone xenograft for implantation into a human.

In another embodiment, the invention provides a method of preparing a bone xenograft for implantation into a human, which includes removing at least a portion of a bone from a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as a corresponding portion of a native bone.

As used herein, the term "portion", as in, for example, a portion of bone or second surface carbohydrate moieties, refers to all or less than all of the respective bone or second surface carbohydrate moieties.

In another embodiment, the invention provides a method of preparing a bone xenograft for implantation into a human, which includes removing at least a portion of a bone from a non-human animal to provide a xenograft; washing the xenograft in water and alcohol; subjecting the xenograft to a cellular disruption treatment; and digesting the xenograft with a glycosidase to remove first surface carbohydrate moieties, whereby the xenograft has substantially the same properties as a corresponding portion of a native bone.

In still another embodiment, this method can include the additional step of treating second surface carbohydrate moieties on the xenograft with capping molecules to cap at least a portion of the second surface carbohydrate moieties.

In yet another embodiment, the invention provides a method of preparing a bone xenograft for implantation into a human, which includes removing at least a portion of a bone from a non-human animal to provide a xenograft; washing the xenograft in water and alcohol; and subjecting the xenograft to sterilization and cellular disruption treatments, whereby the xenograft has substantially the same properties as a corresponding portion of a native bone and is substantially non-immunogenic.

As used herein, the terms "to cap" or "capping", refer to linking a capping molecule such as a carbohydrate unit to the end of a carbohydrate chain, as in, for example, covalently linking a carbohydrate unit to surface carbohydrate moieties on the xenograft.

In further embodiments, the invention provides articles of manufacture including substantially non-immunogenic bone xenografts for implantation into humans produced by the above-identified methods of the invention.

In still a further embodiment, the invention provides a bone xenograft for implantation into a human which includes a portion of a bone from a non-human animal, wherein the portion has substantially no surface carbohydrate moieties which are susceptible to glycosidase digestion, and whereby the portion has substantially the same mechanical properties as a corresponding portion of a native bone.

In yet a further embodiment, the invention provides a bone xenograft for implantation into a human which includes a sterilized, cellular disrupted portion of a bone from a non-human animal, whereby the portion has substantially the same mechanical properties as a corresponding portion of a native bone and is substantially non-immunogenic.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

The present invention is directed against the chronic rejection of xenografts for implantation into humans. Accordingly, the bone xenograft produced in accordance with the method of the invention is substantially non-immunogenic, while generally maintaining the mechanical properties of a native bone.

The bone xenograft may be cut into segments, each of which may be implanted into the recipient as set forth below.

The invention provides, in one embodiment, a method for preparing or processing a xenogeneic bone for engraftment into humans. The bone may be harvested from any non-human animal to prepare the xenografts of the invention. Bone from transgenic non-human animals or from genetically altered non-human animals may also be used as xenografts in accordance with the present invention. Preferably, bovine, ovine, or porcine bones serve as sources of the bone used to prepare the xenografts. More preferably, immature pig, calf or lamb bones are the sources of the bone, since the bone of younger animals consists of more cancellous bone and may be less brittle than that of older animals. Most preferably, the age of the source animal is between six and eighteen months at time of slaughter.

In the first step of the method of the invention, an intact bone portion is removed from a bone of a non-human animal. The source of the bone should be collected from freshly killed animals and preferably immediately placed in a suitable sterile isotonic or other tissue preserving solution. Harvesting of the bone portions should occur as soon as possible after slaughter of the animal and preferably should be performed in the cold, i.e., in the approximate range of about 5° C. to about 20° C., to minimize enzymatic degradation of the bone tissue.

The bone portions are harvested in the cold, under strict sterile technique following known surgical procedures. The harvested bone portion is cut up into strips or blocks and provided with and without cancellous bone attached to cortical bone.

The resultant xenograft is washed in about ten volumes of sterile cold water to remove residual blood proteins and water soluble materials. The xenograft is then immersed in alcohol at room temperature for about five minutes, to sterilize the bone and to remove non-collagenous materials.

After alcohol immersion, the xenograft may be subjected to at least one of the following treatments: radiation treatment, treatment with alcohol, ozonation, one or more cycles of freezing and thawing, and/or treatment with a chemical cross-linking agent. When more than one of these treatments is applied to the xenograft, the treatments may occur in any order.

In one embodiment of the method of the invention, the xenograft may be treated by exposure to ultraviolet radiation for about fifteen minutes or gamma radiation in an amount of about 0.5 to 3 MegaRad.

In another embodiment, the xenograft may be treated by again being placed in an alcohol solution. Any alcohol solution may be used to perform this treatment. Preferably, the xenograft is placed in a 70% solution of isopropanol at room temperature.

In still another embodiment, the xenograft may be subjected to ozonation.

In a further embodiment of the method of the invention, the xenograft may be treated by freeze/thaw cycling. For example, the xenograft may be frozen using any method of freezing, so long as the xenograft is completely frozen, i.e., no interior warm spots remain which contain unfrozen tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes.

In yet a further embodiment, the xenograft may optionally be exposed to a chemical agent to tan or crosslink the proteins within the extracellular matrix, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally to reduce the immunogenicity of the xenograft. For example, aldehydes such as glutaraldehyde, formaldehyde, adipic dialdehyde, and the like, may be used to crosslink the collagen within the extracellular matrix of the xenograft in accordance with the method of the invention. Other suitable crosslinking agents include aliphatic and aromatic diamines, carbodiimides, diisocyanates, and the like.

When glutaraldehyde is used as the crosslinking agent, for example, the xenograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days.

Alternatively, the xenograft can be exposed to a crosslinking agent in a vapor form, including, but not limited to, a vaporized aldehyde crosslinking agent, such as, for example, vaporized formaldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.05 to about 5.0% and a pH of about 7.4, for a period of time which can be from one to fourteen days, and preferably from three to five days. Exposure to vaporized crosslinking agent can result in reduced residual chemicals in the xenograft from the crosslinking agent exposure.

The crosslinking reaction should continue until the immunogenic determinants are substantially removed from the xenogeneic tissue, but the reaction should be terminated prior to significant alterations of the mechanical properties of the xenograft. When diamines are also used as crosslinking agents, the glutaraldehyde crosslinking should occur after the diamine crosslinking, so that any unreacted diamines are capped. After the crosslinking reactions have proceeded to completion as described above, the xenograft should be rinsed to remove residual chemicals, and 0.01–0.05 M glycine may be added to cap any unreacted aldehyde groups which remain.

In addition to or in lieu of the above treatments, the xenograft can be subjected to a cellular disruption treatment to kill the xenograft's cells. Optionally, the cellular disruption treatment can precede or follow digestion of the xenograft with glycosidases to remove surface carbohydrate moieties from the xenograft. According to a further option, the glycosidase digestion in turn can be followed by linkage with capping molecules to cap surface N-acetyllactosamine ends of carbohydrate chains of the xenograft.

In an embodiment of this method of the invention, the xenograft is subjected to a cellular disruption treatment to kill the cells of the bone prior to in vitro digestion of the xenograft with glycosidases. Typically after surface carbohydrate moieties have been removed from nucleated cells and the extracellular matrix, nucleated, i.e., living cells re-express the surface carbohydrate moieties. Re-expression of antigenic moieties of a xenograft can provoke continued immunogenic rejection of the xenograft. In contrast, non-nucleated, i.e., dead cells, are unable to re-express surface carbohydrate moieties. Removal of antigenic surface carbohydrate moieties from the non-nucleated cells and extracellular matrix of a xenograft substantially permanently eliminates antigenic surface carbohydrate moieties as a source of immunogenic rejection of the xenograft.

Accordingly, in the above-identified embodiment, the xenograft of the present invention is subjected to freeze/thaw cycling as discussed above to disrupt, i.e., to kill the cells of the bone. Alternatively, the xenograft of the present invention is treated with gamma radiation having an amount of 0.2 MegaRad up to about 3 MegaRad. Such radiation kills the bone cells and sterilizes the xenograft. Once killed, the bone cells are no longer able to re-express antigenic surface carbohydrate moieties such α-gal epitopes which are factors in the immunogenic rejection of the transplanted xenografts.

In another embodiment of the invention, either before or after the bone cells are killed, the xenograft is subjected to a sterilization treatment. The sterilization treatment includes further immersion in alcohol and or other types of detergents which sterilize the xenograft and optionally remove at least some of the fatty components and/or antigens of the xenograft.

In another embodiment of the invention, either before or after the bone cells are killed, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

The N-acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammals and in New World monkeys (monkeys of South America) as $1 \times 10^6 - 35 \times 10^6$ epitopes per cell, as well as on macromolecules such as proteoglycans of the extracellular matrix. U. Galili et al., *Man, apes, and Old World monkeys differ from other mammals in the expression of α-galactosyl epitopes on nucleated cells*, 263 J. Biol. Chem. 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., *Interaction between human natural anti-α-galactosyl immunoglobulin G and bacteria of the human flora*, 56 Infect. Immun. 1730 (1988); R. M. Hamadeh et al., *Human natural anti-Gal IgG regulates alternative complement pathway activation on bacterial surfaces*, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., *Interaction of the natural anti-Gal antibody with α-galactosyl epitopes. A major obstacle for xenotransplantation in humans*, 14 Immunology Today 480 (1993); M. Sandrin et al., *Anti-pig IgM antibodies in human serum react predominantly with Galα1-3Gal epitopes*, 90 Proc. Natl. Acad. Sci. USA 11391 (1993); H. Good et al., *Identification of carbohydrate structures which bind human anti-porcine antibodies: implications for discordant grafting in man.* 24 Transplant. Proc. 559 (1992); B. H. Collins et al., *Cardiac xenografts between primate species provide evidence for the importance of the α-galactosyl determinant in hyperacute rejection*, 154 J. Immunol. 5500 (1995). Furthermore, xenotransplantation results in major activation of the immune system to produce increased amounts of high affinity anti-Gal. Accordingly, the substantial elimination of α-gal epitopes from bone cells and the extracellular matrix, and the prevention of re-expression of cellular α-gal epitopes can diminish the immune response against the xenograft associated with anti-Gal antibody binding with α-gal epitopes.

Following treatment with glycosidase, the remaining carbohydrate chains (e.g., glycosaminoglycans) of the xenograft are optionally treated with capping molecules to cap at least a portion of the remaining carbohydrate chains. Treatment with capping molecules is applicable to both glycosidase-treated and non-glycosidase-treated xenografts, however. For example, xenografts from knock out animals which may lack α-gal epitopes may be treated with capping molecules to cap carbohydrate moieties on the xenograft, thereby reducing the xenograft's immunogenicity. Examples of capping molecules used in the present invention include fucosyl and n-acetyl glucosamine.

Prior to treatment, the outer lateral surface of the xenograft may optionally be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the outer lateral surface of the xenograft.

Prior to implantation, the bone xenograft of the invention may be treated with limited digestion by proteolytic enzymes such as ficin or trypsin to increase tissue flexibility, or coated with anticalcification agents, antithrombotic coatings, antibiotics, growth factors, or other drugs which may enhance the incorporation of the xenograft into the recipient joint. The bone xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

Further, the bone xenograft of the invention can be treated with an osteoinductive factor in an effective amount to stimulate the conversion of soft tissue cells to osseous tissue formers. Alternatively or additionally, the osteoinductive factor can be administered directly to the target defect. As used herein, the term "osteoinductive factor" refers to a protein which stimulates the differentiation of uncommitted connective tissue cells into bone-forming cells. J. M. Lane et al., Current Approaches to Experimental Bone Grafting, 18 *Orthopedic Clinics of North America* (2) 214 (1987).

Methods of preparing and administering the osteoinductive factor to a graft or to the target defect are known in the prior art such as, for example, Sharon Stevenson, D. V. M., Ph.D., et al., *The Effect of Osteogenic (A Bone Morphogenetic Protein) on the Formation of Bone in Orthotopic Segmental Defects in Rats*, 76, A. The Journal of Bone And Joint Surgery No. 11, 1676–1687 (1994) and John E. Feighan, et al., *Induction of Bone by a Demineralized Bone Matrix Gel: A Study in a Rat Femoral Defect Model*, 13 Journal of Orthopaedic Research 881–889 (1995). For example, osteoinductive factor in the form of a gel, in the presence of a synthetic carrier, such as a hydroxyapatite ceramic cylinder, or using a carrier, such as polyethylene glycol (PEG) or glycerol, or a buffer, such as phosphate, and/or any combination of the above can be administered to the defect site and/or used to impregnate the xenograft.

The osteoinductive factor is added to the interstices of the xenograft and/or to the defect site in an amount effective to induce bone formation. For example, doses of about 10 mg to about 200 mg of osteoinductive factor can be added. Examples of osteoinductive factors which can be used in the present invention include bone morphogenic proteins (BMP) and associated noncollagenous proteins (NCP). Such osteoinductive factors are commercially available from, for example, Creative Biomolecules. Inc., Hopkington, Mass.

The bone xenograft of the invention also can be treated with a demineralization agent in an effective amount to remove substantially minerals such as, for example, calcium from the extracellular matrix of the xenograft. For example, the xenograft of the invention can be soaked in a solution containing demineralization agents, such as, hydrochloric acid, and other demineralization agents known to those of ordinary skill in the art, at a predetermined concentration to demineralize substantially the xenograft of the invention. Once the minerals are removed from the xenograft, a porous volume matrix is formed with pores ranging in size from about 50 microns to about 500 microns. It is theorized that the collagen of demineralized extracellular bone matrix serves as an osteoconductive scaffolding and facilitates the migration of bone forming components once bone graft is implanted. J. M. Lane et al., Current Approaches to Experimental Bone Grafting, 18 *Orthopedic Clinics of North America* (2) 220 (1987). It is further theorized that demineralized bone possesses greater osteoinductive activity than, for example, autologous bone, because bone mineral impedes the release of osteoinductive proteins from extracellular bone matrix. Id. at 218. According to this theory, demineralization enlarges the access of surrounding responsive cells to osteoinductive proteins and augments the potential of the osteoinductive proteins. Such demineralization agents are commercially available from, for example, Sigma, Inc., St. Louis, Mo.

In addition, a binding agent can be added into the bone xenograft of the present invention. As used herein, a binding agent is an adhesion molecule, or adhesive portion or analog thereof, which aids in bone formation by providing a tacky surface to which bone forming cells can stick. The binding agent is added in an effective amount to facilitate the attachment of mesenchymal and other differentiated bone forming cells to the extracellular matrix of the bone xenograft. Examples of binding agents useful in the present invention include bone cement; fibrin glue; mussel glue, such as mussel glue containing bioadhesive polyphenolic proteins derived from several species of the mussel genus Mytilus (see e.g., U.S. Pat. No. 4,585,585); chondronectin; osteonectin; and fibronectin and arginine-glycine-aspartic acid (RGD) peptide (see e.g., U.S. Pat. No. 5,681,353), a portion of which can be conjugated to, for example, chondroitin sulfate, and other binding agents known to those persons of ordinary skill in the art. Such binding agents are commercially available from, for example, Telios Pharmaceuticals, Inc. San Diego, Calif.

The bone xenograft of the invention, or a segment thereof, may be implanted into damaged human joints by those of skill in the art using known arthroscopic surgical techniques. Holes in bones are manually packed with bone according to standard surgical techniques. Specific instruments for performing surgical techniques, which ensure accurate and reproducible placement of bone implants are known to those of skill in the art.

This invention is further illustrated by the following Examples which should not be construed as limiting. The contents of all references and published patents and patent applications cited throughout the application are hereby incorporated by reference.

EXAMPLE 1

Figure 1:
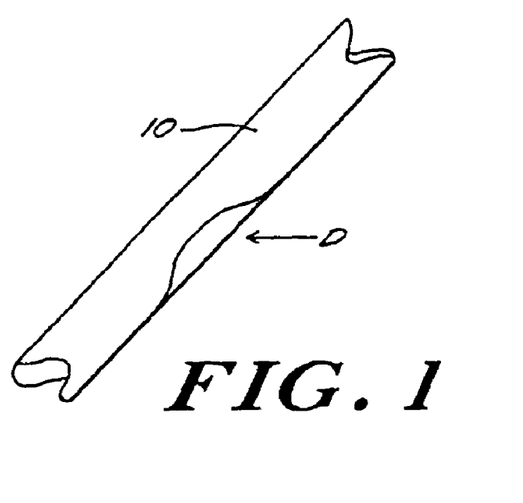
FIG. 1 shows a portion of a bone having a defect.

Assessment of Response in Mice to Implanted Bone Treated with α-Galactosidase and Demineralized Bone Matrix Gel Containing Osteoinductive Factor In this example, porcine bone implants are treated with α-galactosidase to eliminate α-galactosyl epitopes and impregnated with demineralized bone matrix gel containing osteoinductive factor to stimulate the conversion of soft tissue formers in the target defect to osseous tissue formers. The implants are transplanted into mice and the response to the implants is assessed. An exemplary bone portion 10 with a defect D is shown in FIG. 1.

Porcine bone implants are sterilely prepared and surrounding attached soft tissues surgically removed. The bone specimens are washed for at least five minutes with an alcohol, such as ethanol or isopropanol, to remove synovial fluid and lipid soluble contaminants.

The bone specimens are frozen at a temperature ranging from about −35° C. to about −90° C., and preferably at a temperature up to about −70° C., to disrupt, that, is to kill, the specimens' bone cells.

Each bone specimen is cut into two portions. The first bone portion is immersed in a buffer solution containing α-galactosidase at a predetermined concentration. The first bone portion is allowed to incubate in the buffer solution for a predetermined time period at a predetermined temperature. The second bone portion is incubated under similar conditions as the first bone portion in a buffer solution in the absence of α-galactosidase and serves as the control.

At the end of the incubation, the bone portions are washed under conditions which allow the enzyme to diffuse out. Assays are performed to confirm the complete removal of the α-gal epitopes.

The α-galactosidase first bone portions disclosed above are then impregnated with demineralized bone matrix gel containing osteoinductive factor prepared according to methods known in the prior art, such as, for example, John E. Feighan, et al, *Induction of Bone by a Demineralized Bone Matrix Gel: A Study in a Rat Femoral Defect Model*, 13 Journal of Orthopaedic Research 881–889 (1995).

Figure 2:
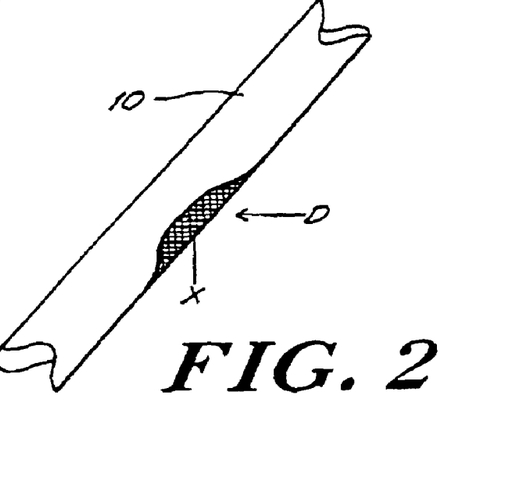
FIG. 2 shows the bone portion of FIG. 1 with a xenograft of the invention in the defect.

The bone samples are implanted in subcutaneous tissues of mice under general inhalation anesthesia following known surgical procedures. Bone is implanted in subcutaneous tissues to evaluate the osteoinductive properties of bone. Any bone formed is evidence of osteoinductive properties. Osteoconductive properties of bone xenograft are evaluated after the xenograft is implanted using bone defective models such as the long bone drill hole model. The implantation procedure is performed under sterile surgical technique, and the wounds are closed with 3-0 vicryl or a suitable equivalent known to those of ordinary skill in the art. FIG. 2 shows the bone portion 10 with the xenograft X (shown crosshatched) in place at the defect D. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-bone xenograft antibodies (i.e. antibodies binding to antigens other than the α-gal epitopes) in serum samples from the transplanted mice. Blood samples are drawn from the transplanted mice on the day of implant surgery and at periodic (e.g., two week) intervals post-transplantation. The blood samples are centrifuged and the serum samples are frozen and evaluated for the anti-Gal and other non-anti-Gal anti-bone xenograft antibody activity.

Anti-Gal activity is determined in the serum samples in ELISA with α-gal-BSA as solid phase antigen, according to methods known in the prior art, such as, for example, the methods described in Galili et al., *Porcine and bovine cartilage transplants in cynomolgus monkey: II. Changes in anti-Gal response during chronic rejection*, 63 Transplantation 645–651 (1997).

Assays are conducted to determine whether α-galactosidase treated xenografts induce the formation of anti-bone xenograft antibodies. For measuring anti-bone xenograft antibody activity, an ELISA assay is performed according to methods known in the prior art, such as, for example, the methods described in K. R. Stone et al., *Porcine and bovine cartilage transplants in cynomolgus monkey: I. A model for chronic xenograft rejection*, 63 Transplantation 640–645 (1997).

The bone xenografts are optionally explanted at one to two months post-transplantation, sectioned and stained for histological evaluation of inflammatory infiltrates. Post-transplantation changes in anti-Gal and other anti-bone xenograft antibody activities are correlated with the inflammatory histologic characteristics (i.e., granulocytes or mononuclear cell infiltrates) within the explanted bone, one to two months post-transplantation, using methods known in the art, as, for example, the methods described in K. R. Stone et al., *Porcine and bovine cartilage transplants in cynomolgus monkey: I. A model for chronic xenograft rejection*, 63 Transplantation 640–645 (1997).

Where the bone xenograft is explanted, the bone xenograft is aseptically harvested, using anesthetic procedure, removal of the implant and closure of the soft tissue. Tissue is harvested for possible immunologic testing if the gross and histopathologic evaluation of the transplants indicate good performance of the transplanted bone. The xenograft samples are collected, processed, and examined microscopically. A portion of the implant and surrounding tissue is frozen in an embedding medium for frozen tissue specimens in embedding molds for immunohistochemistry evaluation according to the methods known in the prior art. "TISSUE-TEK®" O.C.T. compound which includes 10.24% w/w polyvinyl alcohol, 4.26% w/w polyethylene glycol, and 86.60% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 2

Assessment of Primate Response to Implanted Bone Treated with α-Galactosidase and Demineralized Bone Matrix Gel Containing Osteoinductive Factor In this example, porcine bone implants are treated with α-galactosidase and demineralized bone matrix gel containing osteoinductive factor, the implants are transplanted into cynomolgus monkeys, and the primate response to the bone implants is assessed, as described in Example 1. After the bone xenografts are explanted and tissue is harvested for possible immunologic testing, the animals are allowed to recover and are monitored closely until the incisions have healed and the gait of the animals is normal.

EXAMPLE 3

Assessment of Response in Mice to Implanted Bone Treated with α-Galactosidase, Demineralized Bone Matrix Gel Containing Osteoinductive Factor, Fucosyl and Fucosyltransferase In this example, porcine bone implants are treated with α-galactosidase to eliminate α-gal epitopes, as described in Example 1. The implants are further treated with fucosyl and fucosyl transferase to cap carbohydrate chains with fucosyl. Fucosyltransferase facilitates the transfer of fucosyl to the xenograft. The fucosyl links to and thus caps the carbohydrate chains. Capping with fucosyl interferes with the ability of the subject's immune system to recognize the xenograft as foreign. The implants are transplanted into mice, and the response to the bone implants is assessed.

Porcine bone implants are prepared as described in Example 1 including the α-galactosidase treatment. Prior to implantation into the mice, however, the implants are further treated with a predetermined amount of fucosyl and fucosyltransferase, at specified concentrations for a predetermined time and at a predetermined temperature, to cap carbohydrate chains with fucosyl. For example, the samples are immersed in a buffer solution at predetermined concentrations of fucosyl and fucosyl transferase. The samples are incubated for a predetermined time period at a predetermined temperature.

Other molecules, such as n-acetyl glucosamine in combination with the corresponding glycosyltransferase, can also be used for capping the carbohydrate chains of the implants.

Subsequently, the samples are washed to remove the enzyme and implanted into the mice, and the occurrence of an immune response against the xenograft is assessed as described above in Example 1.

EXAMPLE 4

Assessment of Primate Response to Implanted Bone Treated with α-Galactosidase, Demineralized Bone Matrix Gel Containing Osteoinductive Factor; Fucosyl and Fucosyltransferase In this example, porcine bone implants are treated with α-galactosidase, demineralized bone matrix gel containing osteoinductive factor, fucosyl and fucosyltransferase; the implants are transplanted into cynomolgus monkeys and the primate response to the bone implants is assessed, as described above in Examples 1, 2 and 3.

EXAMPLE 5

Assessment of Response in Mice to Implanted Bone Treated with Alcohol and Freeze/Thaw Cycling In this example, porcine bone implants are treated with alcohol and freeze/thaw cycling prior to their transplantation in mice and the response of the mice to the implants is assessed.

Porcine bone implants are sterilely prepared and surrounding attached soft tissues surgically removed. The resultant xenograft is washed in about ten volumes of sterile cold water to remove residual blood proteins and water soluble materials. The xenograft is then immersed in alcohol at room temperature for about five minutes, to sterilize the bone and to remove non-collagenous materials.

After the alcohol washing, the xenograft is treated by again placing the xenograft in an alcohol solution of 70% isopropanol at room temperature for at least five minutes.

Following the alcohol treatment step, the bone implants are placed in a freezer until the xenograft is completely frozen, i.e., no interior warm spots remain which contain unfrozen tissue. Each bone implant is then thawed by immersion in an isotonic saline bath at room temperature (about 25° C.) for about ten minutes.

It should be understood that the bone implants alternatively can be subjected to the above-described freeze/thaw cycling treatment prior to the alcohol treatment step.

The implants are then implanted in the mice and the occurrence of an immune responses against the xenograft is assessed as described above in Example 1.

EXAMPLE 6

Assessment of Primate Response to Implanted Bone Treated with Alcohol and Freeze/Thaw Cycling In this example, porcine bone implants are treated with alcohol and freeze/thaw cycling prior to their transplantation in cynomolgus monkeys and the primate response to the implants is assessed as described above in Examples 1–5.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. An article of manufacture comprising a substantially non-immunogenic bone xenograft for implantation into a human, produced by the process of
   a. removing at least a portion of a bone from a non-human animal to provide a xenograft;
   b. washing the xenograft in water and alcohol;
   c. subjecting the xenograft to a cellular disruption treatment; and
   d. digesting the xenograft with a glycosidase to remove a plurality of first surface carbohydrate moieties,
whereby the xenograft has substantially the same mechanical properties as a corresponding portion of a native bone.

2. The article of manufacture of claim 1, further comprising the step of
   prior to step c, piercing the xenograft.

3. The article of manufacture of claim 1, further comprising the step of
   following step c, treating the xenograft with a second enzyme.

4. The article of manufacture of claim 3 wherein the second enzyme is selected from the group consisting of ficin and trypsin.

5. The article of manufacture of claim 1, further comprising the step of
   following step c, treating the xenograft with one or more agents selected from the group consisting of anticalcification agents, antithrombotic agents, antibiotics, and growth factors.

6. The article of manufacture of claim 1, further comprising the step of
   following step c, sterilizing the xenograft.

7. The article of manufacture of claim 6 wherein the sterilizing step is selected from the group consisting of treatment with glutaraldehyde, treatment with formaldehyde, treatment with ethylene oxide, and treatment with propylene oxide.

8. The article of manufacture of claim 1, further comprising the step of
   following step d, treating a plurality of second surface carbohydrate moieties on the xenograft with a plurality of capping molecules to cap at least a portion of the second surface carbohydrate moieties,
whereby the xenograft is substantially non-immunogenic.

9. The article of manufacture of claim 8, wherein at least a portion of the capping molecules are a plurality of fucosyl molecules.

10. The article of manufacture of claim 8, wherein at least a portion of the capping molecules are a plurality of n-acetyl glucosamine molecules.

11. The article of manufacture of claim 1, wherein the glycosidase is a galactosidase.

12. The article of manufacture of claim 11, wherein the galactosidase is an α-galactosidase molecule.

13. The article of manufacture of claim 1, wherein the cellular disruption treatment comprises freeze/thaw cycling.

14. The article of manufacture of claim 1, wherein the cellular disruption treatment comprises exposure to gamma radiation.

15. The article of manufacture of claim 1 further comprising the step of
   following step c, exposing the xenograft to a crosslinking agent in a vapor form.

16. The article of manufacture of claim 1 further comprising the step of
   following step c, treating the xenograft with a demineralization agent to remove substantially minerals from an extracellular matrix.

17. The article of manufacture of claim 1 further comprising the step of
   following step c, adding an osteoinductive factor to the xenograft.

18. The article of manufacture of claim 1 further comprising the step of
   following step c, adding a binding agent to the xenograft.

19. An article of manufacture comprising a substantially non-immunogenic bone xenograft for implantation into a human, produced by the process of
   a. removing at least a portion of a bone from a non-human animal to provide a xenograft;
   b. washing the xenograft in water and alcohol; and
   c. subjecting the xenograft to at least one treatment selected from the group consisting of exposure to ultraviolet radiation, immersion in alcohol, ozonation, and freeze/thaw cycling,
whereby the xenograft has substantially the same mechanical properties as a corresponding portion of a native bone and is substantially non-immunogenic.

20. The article of manufacture of claim 19, wherein the treatment comprises immersion in alcohol and freeze/thaw cycling.

21. An article of manufacture comprising a substantially non-immunogenic bone xenograft for implantation into a human, produced by the process of
   a. removing at least a portion of a bone from a non-human animal to provide a xenograft;
   b. washing the xenograft in water and alcohol; and
   c. subjecting the xenograft to a sterilization treatment and a cellular disruption treatment,
whereby the xenograft has substantially the same mechanical properties as a corresponding portion of a native bone and is substantially non-immunogenic.

22. The article of manufacture of claim 21 wherein the cellular disruption treatment comprises freeze-thaw cycling.

23. The article of manufacture of claim 21 wherein the sterilization treatment comprises immersion in alcohol.

24. A method of preparing a bone xenograft for implantation into a human, which comprises
   a. removing at least a portion of a bone from a non-human animal to provide a xenograft;
   b. washing the xenograft in water and alcohol;
   c. subjecting the xenograft to a cellular disruption treatment; and
   d. digesting the xenograft with a glycosidase to remove a plurality of first surface carbohydrate moieties,
   whereby the xenograft has substantially the same mechanical properties as a corresponding portion of a native bone.

25. The method of claim 24, further comprising the step of
   prior to step c, piercing the xenograft.

26. The method of claim 24, further comprising the step of
   following step c, treating the xenograft with a second enzyme.

27. The method of claim 26 wherein the second enzyme is selected from the group consisting of ficin and trypsin.

28. The method of claim 24, further comprising the step of
   following step c, treating the xenograft with one or more agents selected from the group consisting of anticalcification agents, antithrombotic agents, antibiotics, and growth factors.

29. The method of claim 24, further comprising the step of
   following step c, sterilizing the xenograft.

30. The method of claim 29, wherein the sterilizing step is selected from the group consisting of treatment with glutaraldehyde, treatment with formaldehyde, treatment with ethylene oxide, and treatment with propylene oxide.

31. The method of claim 24, further comprising the step of
   following step d, treating a plurality of second surface carbohydrate moieties on the xenograft with a plurality of capping molecules to cap at least a portion of the second surface carbohydrate moieties,
whereby the xenograft is substantially non-immunogenic.

32. The method of claim 31, wherein at least a portion of the capping molecules are a plurality of fucosyl molecules.

33. The method of claim 31, wherein at least a portion of the capping molecules are a plurality of n-acetyl glucosamine molecules.

34. The method of claim 24, wherein the glycosidase is a galactosidase.

35. The method of claim 34, wherein the galactosidase is an α-galactosidase.

36. The method of claim 24, wherein the cellular disruption treatment comprises freeze/thaw cycling.

37. The method of claim 24, wherein the cellular disruption treatment comprises exposure to gamma radiation.

38. The method of claim 24 further comprising the step of
   following step c, exposing the xenograft to a crosslinking agent in a vapor form.

39. The method of claim 24 further comprising the step of
   following step c, treating the xenograft with a demineralization agent to remove substantially minerals from an extracellular matrix.

40. The method of claim 24 further comprising the step of
   following step c, adding an osteoinductive factor to the xenograft.

41. The method of claim 24 further comprising the step of
   following step c, adding a binding agent to the xenograft.

42. A method of preparing a bone xenograft for implantation into a human, which comprises
   a. removing at least a portion of a bone from a non-human animal to provide a xenograft;
   b. washing the xenograft in water and alcohol; and
   c. subjecting the xenograft to at least one treatment selected from the group consisting of exposure to ultraviolet radiation, immersion in alcohol, ozonation, and freeze/thaw cycling,
   whereby the xenograft has substantially the same mechanical properties as a corresponding portion of a native bone and is substantially non-immunogenic.

43. The method of claim 42, wherein the treatment comprises immersion in alcohol and freeze/thaw cycling.

44. A method of preparing a bone xenograft for implantation into a human, which comprises
   a. removing at least a portion of a bone from a non-human animal to provide a xenograft;
   b. washing the xenograft in water and alcohol; and
   c. subjecting the xenograft to a sterilization treatment and a cellular disruption treatment,
   whereby the xenograft has substantially the same mechanical properties as a corresponding portion of a native bone and is substantially non-immunogenic.

45. The method of claim 44, wherein the cellular disruption treatment comprises freeze/thaw cycling.

46. The method of claim 44, wherein the sterilization treatment comprises immersion in alcohol.

* * * * *